(12) United States Patent
Konkoy et al.

(10) Patent No.: US 6,800,657 B2
(45) Date of Patent: Oct. 5, 2004

(54) SUBSTITUTED 5-OXO-5, 6, 7, 8-TETRAHYDRO-4H-1-BENZOPYRANS

(75) Inventors: Christopher S. Konkoy, Georgetown, TX (US); David B. Fick, Mission Viejo, CA (US); Sui Xiong Cai, San Diego, CA (US); Nancy C. Lan, Altadena, CA (US); John F. W. Keana, Eugene, OR (US)

(73) Assignee: Euro-Celtique S.A., Luxembourg (LU)

( * ) Notice: Subject to any disclaimer, the term of this patent is extended or adjusted under 35 U.S.C. 154(b) by 52 days.

(21) Appl. No.: 10/610,871

(22) Filed: Jul. 2, 2003

(65) Prior Publication Data
US 2004/0097581 A1 May 20, 2004

Related U.S. Application Data

(62) Division of application No. 09/980,628, filed as application No. PCT/US00/15307 on Jun. 5, 2000, now Pat. No. 6,680,332.
(60) Provisional application No. 60/137,501, filed on Jun. 4, 1999, now abandoned.

(51) Int. Cl.$^7$ ........................ A61K 31/38; C07D 311/76
(52) U.S. Cl. ........................ 514/456; 549/404
(58) Field of Search ........................ 514/456; 549/404

(56) References Cited

FOREIGN PATENT DOCUMENTS

| DE | 44 30 639 A1 | 3/1998 |
|---|---|---|
| WO | WO 95/21612 A3 | 8/1995 |
| WO | WO 95/21612 A2 | 8/1995 |
| WO | WO 97/43272 A3 | 11/1997 |
| WO | WO 97/43272 A2 | 11/1997 |

OTHER PUBLICATIONS

Abdel–Latif, F.F., et al., "Synthesis of Heterocycles Through Reactions of Nucleophiles with Acrylonitriles, Part15: Synthesis of Some New Functionalized Benzo [*b*] Pyrans of Potential Biological Activity," *J. Chem. Res.* 5:1220–1228, Chemical Society (1995).

(List continued on next page.)

*Primary Examiner*—D. Margaret Seaman
*Assistant Examiner*—Raymond Covington
(74) *Attorney, Agent, or Firm*—Sterne, Kessler, Goldstein & Fox, P.L.L.C.

(57) ABSTRACT

Disclosed is a method for treating a disorder responsive to the positive modulation of AMPA receptors in animals suffering therefrom, comprising administering to an animal in need thereof a compound of Formula I:

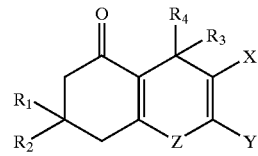

or a pharmaceutically acceptable salt or prodrug thereof, wherein:

Y is $NH_2$, NHR, and NHCOR; Z is O and S; and $R_1$, $R_2$, $R_3$, $R_4$, and X are defined herein. These compounds can be used as cognitive enhancers, for the treatment of neurodegenerative diseases, including Alzheimer's disease, amyotrophic lateral sclerosis, Huntington's disease, Parkinson's disease, AIDS associated dementia and Down's syndrome as well as for the treatment of schizophrenia and myoclonus. Also disclosed are pharmaceutical compositions useful for treating disorders responsive to the positive modulation of AMPA receptors, and novel compounds of Formula I.

18 Claims, 1 Drawing Sheet

OTHER PUBLICATIONS

Abdel–Latif, F.F., et al., "Synthesis of Heterocycles Through Reactions of Nucleophiles with Acrylonitriles, Part 15: Synthesis of Some New Functionalized Benzo [*b*] Pyrans and Indeno [1, 2–*b*] Pyrans of Potential Biological Activity," *J. Chem. Res.* 5:178–179, Chemical Society (1995).

Abdel–Latif, F.F., et al., "Synthesis of Some Heterocyclic Compounds Via the Ternary Condensation with 3–Acetylpyridine," *Heterocyclic Commun.* 3:245–252, Freund Publishing House, Ltd. (1997).

Al–Ashmawi, M.I., et al., "Ammonolysis and Acylation of Some Novel B–Enaminonitriles," *Egypt. J. Pharm. Sci.* 33:849–858, The National Information and Documentation Centre (1992).

Al–Ashmawi, M.I., et al., "1.3–Diketones as Oxydianions in Michael Type Reactions," *Zhonghua Yaoxue Zazhi* 44:241–247, Amvo Publishing Company (1992).

Al–Omran, F., et al., "new Spiropyran–4–Ylindolidine Derivatives from the Reaction of 2–Oxo–3–Cyanomethlidene–2, 3–Dihydroindoles with Cyclohexanediones and Phenols," *Org. Prep. Proced. Intl.* 30:363–366, Organic Preparation and Procedures, Inc. (Jun. 1998).

Copani, A., et al., "Nootropic Drugs Positively Modulate α–Amino–3–Hydroxy–5–Methyl–4–Isoxazolepropionic Acid–Sensitive Glutamate Receptors in Neuronal Cultures," *J. Neurochem.* 58:119–1204, Raven Press (1992).

Desai, M.A., et al., "1–BCP, a Memory–enhancing Agent, Selectively potentiates AMPA–induced [$^3$H]Norepinephrine Release in Rat Hippocampal Slices," *Neuropharm,* 34:141–147, Pergamon Press (1995).

Dworczak, R., et al., "Über Spiro [indan–pyrane] und Inden–propellane—Addukte von 1,3–Dicarbonylverbindungen an 2–(Dicyanmethylen)–1, 3–indandion," *Chem. Ber.* 122:1323–1328, VCH Verlagsgesellschaft mbH. (1989).

Dyachenko, V.D., et al., "Synthesis and Alkylation of 3–Cyano–4, 7, 7–Timethyl–2–Thioxo–1, 2, 3, 4, 5, 6, 7, 8–Octahydroquinolin–5–one," *Russ. J. Org. Chem.* 34:707–711, Manka Hayka/Interperiodica Publishing (May 1998).

Dyachenko, V.D. and Litvinov, V.P., "Synthesis of N–Methylmorpholinium 6–Amino–4–Aryl–3, 5–di–Cyano–1, 4–Dihydropyridine–2–Thiolates by the Michael Reaction," *Russ. J. Org. Chem.* 34:554–556, Manka Hayka/Interperiodica Publishing (Apr. 1998).

Dyachenko, V.D., et al., "Convenient Method for Synthesis of Functionally Substituted Hexahydroquinolines. Molecular and Crystal Structure of 4–Isopropyl–7, 7–Dimethyl–5–Oxo–3–Cyano–2–Cyanomethylthio–1, 4, 5, 6, 7, 8–Hexahydroquinoline," *Chem. Hetero. Compds.* 33:684–690, Consultants Bureau (1997).

Dyachenko, V.D., et al., "Synthesis and Reactions of 6–Amino–1, 4–Dihydro–3, 5–Dicyano–4–Cyclohexanespiropyridine–2–Selenol," *Dokl. Akad. Nauk.* 355:62–65, Maik Nauka (1997).

Elnagdi, M.H., et al., "Synthesis of Condensed 4H–Pyrans: The Reaction of 1, 1–Dimethyl–3, 5–Diketocyclohexane with Cinnamonitriles," *J. Prakt. Chemie.* 331:971–976, VEB J.A. Barth (1989).

Gomaa, M.A.–M., "Reaction of 2–(3–Methyl–5–Oxo–1–Phenyl–1H–Pyrazol–4 (5H)–ylidene) Propanedinitrile with 1,3–Dicarbonyl Compounds," *Pharmazie* 54:352–354, Govi–Verlag (Apr. 1999).

Goncharenko, M.P., et al., "Cyclization Reactions of Nitriles. XXVII. The Structure and Comformationally Ambient Heterocyclization of Substituted 2–(2–Thiocarbamoyl–2–Cyanoethyl)–3–Oxo–1– Cyclohexenolates," *J. Org. Chem. USSR* 26:1362–1370, Consultants Bureau (1990).

Gudrinietse, É.Y., et al., "Condensation of Dicarbonyl Compounds with Malonitrile. X. 2–Formyldimedone in Reaction with Malonitrile," *J. Org. Chem. USSR* 18:2089–2091, Consultants Bureau (1983).

Hassanien, A.A., et al., "Utility of 2–Amino–4,5,6, 8–Tetrahydro–7*H*–Chromene–3–Carbonitriles in Synthesis of Chromeno [2,3–*d*] Pyrimidine and Chromeno [3,2–*e*] [1, 2, 4]Triazolo[1,5–*c*]Pyrimidine Derivatives of Pharmaceutical Interest," *J. Indian Chem. Soc.* 76:350–354, The Indian Chemical Society (Apr. 1999).

Higashiyama, K. and Otomasu, H., "Spiro Heterocyclic Compounds. III. Synthesis of Spiro[Oxindole–3, 4'–(4'*H*–Pyran)] Compounds," *Chem. Pharm. Bull.* 28:648–651, Pharmaceutical Society of Japan (1980).*

Ikeda, A., et al., "Clinical Trial of Piracetam in Patients with Myoclonus: Nationwide Multiinstitution Study in Japan," *Movement Dis.* 11:691–700, Lippincott–Raven (1996).*

Joshi, K.C., et al., "Spiro Heterocycles. Part–XIX. Synthesis and Insecticidal Activity of Some New Fluorine–containing Spiro[4*H*–1–Benzo–Pyran–4, 3'–[3*H*]—Indole]–3–Carbonitriles/Carboxyethylesters," *J. Indian Chem. Soc.* 67:490–492, The Indian Chemical Society (1990).*

Junek, H. and Aigner, H., "Chromene und Chinoline durch Tetracyanalkylierung von Cyclischen 1.3–Diketonen," *Z. Naturforschung B*25:1423–1426, Verlag der Zeitschrift für Naturforschung Tübingen (1970).

Kandeel, Z.E., et al., "Studies with 1,3–Diketones: A Convenient Synthesis of Some Tetrahydro–4H–benzopyran and Tetrahydroquinoline Derivatives," *Heteroatom Chem.* 7:35–38, John Wiley & Sons, inc. (1996).

Kayukova, O.V., et al., "6.6–Dimethyl–4,8–Dioxospiro[2.5] Octane–1,1,2,2–Tetra–Carbonitrile in the Synthesis of Heterocyclic Compounds of the 2,3–Dihydrofuran and 5,6,7, 8–Tetradydro–4H–Chromene Series," *Chem. Hetero. Compds.* 34:148–158, Consultants Bureau (Aug. 1998).

Khodeir, M., et al., "Polyfunctionally Substituted Heterocycles: Routes to 4H–Naphtho–[2,3–b]pyrans, Pyridines and 4H–Naphtho[1,2–b]Pyrano[2,3–d]Pyrimidines," *Pharmazie* 47:486–487, Govi–Verlag (1992).

Kislyi, V.P., et al., "Heterocycles with a β–nitroenamine Fragment 1. Synthesis of 2–Amino–3–Nitropyrans from Nitroacetonitrile. Crystal and Molecular Structure of 2–Amino–4–(4–Fluorophenyl)–3–Nitro–7, 7–Dimethyl–5, 6,7,8,–Tetrahydrochromen–5(4*H*)–one," *Russ. Chem. Bell.* 48:1131–1134, Consultants Bureau (Jun. 1999).

Larson, J., et al., "Effects of an AMPA Receptor Modulator on Methamphetamine–Induced hyperactivity in Rats," *Brain Res.* 738:353–356, Elsevier Science B.V. (1996).

Leeson, P.D. and Iversen, L.L., "The Glycine Site on the NMDA Receptor: Structure–Activity Relationships and Therapeutic Potential," *J. Med. Chem.* 37:4053–4067, American Chemical Society (1994).

Martín, N., et al., "on the Cyclization to the Elusive Amino–4*H*–pyran Ring Some New Facts," *Liebigs Ann. Chem.* 1990:101–104, VCH Verlagsgesellschaft mbH. (1990).

Metchkov, T.D., et al., "Interaction of 1–Nitro–2–Arylacrylonitriles with Dimedone to Chromene Derivatives," *Dokl. Bolg. Akad. Nauk.* 39:51–53, Maik Nauka (1986).

Okamoto, Y., et al., "A Short Three Components Approach to Fused Pyrrolo[2,3–b]Pyrrolidinone," *Heterocycles* 43:2353–2356, Sendai Institute of Heterocyclic Chemistry (1996).

Okamoto, Y., et al., "Simple Preparation of Fused Pyrrolo [2,3–*b*]Pyrrolidinones and Pyrrolo[2,3–c]Pyridazinones," *J. Chem. Soc. Perkin Trans. 1* 9:1323–1327, Chemical Society (1997).

Polyanskaya, A.S. et al., "Synthesis of Substituted 4H, 6H, 8H–Chromene and 4H–Pyrazolo[3,4–b]–Pyran," *J. Org. Chem. USSR* 20:2260–2261, Consultants Bureau (1984).

Rappoport, Z. and Ladkani, D., "Nucleophilic Attacks on Carbon–Carbon Double Bonds. Part XX. Reaction of Active Methylene Compounds with Electrophilic Olefins. Formation of Substituted 2–Amino–4–cyano–4*H*–pyrans," *J. Chem. Soc. Perkin Trans. 1* 22:2595–2601, Chemical Society (1974).

Sadek, K.U., et al., "Nitriles in Heterolcyclic Synthesis: the Reaction of Ethyl 2–Oxoindoliden–3–ylidene Cyanoacetate and of 3–Dicyanoethlideneindoliden–2–one with Phenols and Amines," *J. Heteroatom Chem.* 6:597–600, John Wiley & Sons, inc. (1995).

Sharanin, Y.A., "Cyclization Reactions of Nitriles. II. Reaction of Arylidene and Furfuylidene Derivatives of Malononitrile with Oxaloacetic Ester," *J. Org. Chem. USSR* 16:1866–1870, Consultants Bureau (1980).

Sharanin, Y.A., et al., "Cyclization Reactions of Nitriles. IV. Reaction of Arylidenemalononitriles with 1,3–Dicarbonyl Compounds," *J. Org. Chem USSR* 18:544–548, Consultants Bureau (1982).

Sharanin, Y.A., et al., "Cyclization Reactions of Nitriles. VI. Synthesis of 2–Amino–4–(2–Furyl)–4H–Pyrans," *J. Org. Chem. USSR* 19:150–158, Consultants Bureau (1983).

Sharanin, Y.A. and Goncharenko, M.P., "Synthesis and Recyclization of 2–Amino–4–Aryl–7, 7–Dimethyl–5–Oxo–3–Carbamoyl–5,6,7, 8–Tetrahydro–4H–Benzo[b] Pyrans," *J. Org. Chem. USSR* 24:408–410, Consultants Bureau (1988).

Sharanin, Y.A. and Shestopalov, A.M., "Cyclization of Nitriles. XXXIV. Transformation of 4–Aryl–2,6–Diamino–3,5–Dicyano–4H–Thiopyrans into Substituted 4–Aryl–3–Cyano–2 (1H)–Pyridinethiones and 2–Amino–4–Aryl–7,7–Dimethyl–5–Oxo–3–Cyano–5,6,7, 8–Tetrahydro–4H–Benzo[b] Pyrans," *J. Org. Chem. USSR* 25:1196–1200, Consultants Bureau (1989).

Sharanina, L.G., et al., "Cyclization of Nitriles. XX. Synthesis of Condensed 2–Amino–4H–Pyrans and the Molecular Structure of 2–Amino–7,7–Dimethyl–4– (3–Fluorophenyl)–5–Oxo–3–Ethoxycarbonyl–5,6,7, 8–Tetrahydro–4H–Benzo[b]Pyran," *J. Org. Chem. USSR* 22:1185–1191, Consultants Bureau (1986).

Siaka, S., et al., "Reaction of Polycyanocyclopropanes with Amine Hydroiodides," *Russ. J. Org. Chem.* 34:1269–1276, Hayka/Interperiodica (1998).

Singh, K., et al., "A Synthetic Entry into Fused Pyran Derivatives Through Carbon Transfer Reactions of 1,3–Oxazinanes and Oxazolidines With Carbon Nucleophiles," *Tetrahedron* 52:14273–14280, Pergamon Press (1996).

Staubli, U., et al., "Facilitation of Glutamate Receptors Enhances Memory," *Proc. Natl. Acad. Sci. USA* 91:777–781, National Academy of Sciences (1994).

Thomas, R.J., "Excitatory Amino Acids in Health and Disease," *J. Am. Ger. Soc.* 43:1279–1289, Williams & Wilkins (1995).

Vilsmaier, E. and Baumheier, R., "[4 + 2]–Cycloadditionen von 2–Cyclopropyliden–1,3–dinen mit Elektronenreichen Alkinen," *Chem. Ber.* 122:1285–1290, VCH Verlagsgesllschaft mbH. (1989).

Wamhoff, H., "Dihalogentriphenylphosphorane in der Heterocyclensynthese; $27^1$:Heterokondensierte 1,2,4–Trianzolo [1,5–*c*] Pyrimidine aus Enaminonitrilen via O–Ethylformimide," *Synthesis* 11:1129–1132, Thieme Stuttgart (1993).

Yamada, K.A. and Turetsky D.M., "Allosteric Interactions Between Cyclothiazide and AMPA/kainate Receptor Antagonists," *Brit. J. Pharm.* 117:1663–1672, Stockton Press (1996).

Zivkovic, I., et al., "7–Chloro–3–Methyl–3–4–Dihydro–2H–1,2,4 Benzothiadiazine S,S,–Dioxide (IDRA 21) : A Benzothiadiazine Derivative that Enhances Cognition by Attenuating DL–α–Amino–2, 3–Dihydro–5–Methyl–3–Oxo–4–Isoxazolepropanoic Acid (AMPA) Receptor Desensitization," *J. Pharm. Exp. Therap.* 272:300–309, WIlliams & Wilkins (1995).

STN Easy, Accession No. 1989:477769, English language abstract of Dworczak, R., et al., "Syntheses with nitriles. LXXXII. on Spiro[Indan–pyrans] and Indene–Propellanes—Adducts of 2–(Dicyanomethylene)–1,3–Indandione with 1,3–Dicarbonyl Compounds" *Chem. Ber.* 122:1323–1328, VCH Verlagsgesellschaft mbH. (1989) (Document AT3).

STN Easy, Accession No. 1997:788782, English language abstract of Dyachenko, V.D., "Synthesis and Reactions of 6–Amino–1,4–Dihydro–3, 5–Dicyano–4–Cyclohexanespiropyridine–2–Selenol," *Dokl. Akad. Nauk.* 355:62–65, Maik Nauka (1997) (Document AS4).

STN Easy, Accession No. 1989:477804, English language abstract of Vilsmaier, E., "[4 + 2] Cycloaddition Reactions of 2–Cyclopropylidene–1,3–Diones with Electron–Rich Alkynes," *Chem. Ber.* 122:1285–1290, VCH Verlagsgesellschaft mbH. (1989) (Document AR16).

Dialog File 72, Accession No. 1993334308, English language abstract for Wamhoff, H., et al., "Dihalogentriphenylphosophorane in Heterocyclene Synthesis. Part 27.: Heterocondensed 1,2,4–Triazolo(1,5–c)pyrimidene from Enamic Nitriles, via O–Ethylformides," *Synthesis* 11:1129–1132, Thieme Stuttgart (1993) (Document AS16).

Dialog FIle 351, Accession No. 10643248, Derwent WPI English language abstract for DE 44 30 639.

Caplus Database, Accession No. 1978:443024, Chemical Structure Disclosure for Sokolova, L.N., et al., "Chemistry of Cyanonitroalkenes. II. Synthesis and Structure of Heterylcyanonitroalkenes," *XXX Gertsenovsk. Chteniya. Khimiya* 59–63, (1977).

Junek, H. and Aigner, H., "Synthesis with Nitriles. XXXI. Chromenes and Quinolines by Tetracyanoalkylation of Cyclic 1,3–Diketones," *Chem. Abstracts 74*:335, Abstract No. 53469u, Chemical Abstract Service (1971) (Document AR8).

International Search Report for International Patent Application No. PCT/US00/15307, mailed Oct. 13, 2000.

Dickinson, G., "Recent Developments in the Diagnosis and Treatment of AIDS and Related Syndromes," *18th Ann. Meet. of the Med. Sect. Am. Counc. Life Insurance*, pp. 41–52, American Council for Life Insurance (1993).

Füst, G., "Recent Developments in Research of HIV Infection—A State of Art," *Acta Microbiol. et Immunol. hung. 41*:5–21, National Institute of Haematology (1994).

Huff, J.R., "HIV Protease: A Novel Chemotherapeutic Target for AIDS," *J.Med. Chem. 34*:2305–2314, American Chemical Society (1991).

* cited by examiner

SUBSTITUTED 5-OXO-5, 6, 7, 8-TETRAHYDRO-4H-1-BENZOPYRANS

The present application is a divisional of U.S. patent application Ser. No. 09/980,628, filed May 20, 2002 now U.S. Pat. No. 6,680,332, which is a national phase of PCT/US00/15307, with an international filing date of Jun. 5, 2000, published in English under PCT Article 21(2), now abandoned, which claims priority benefit under 35 U.S.C. 119(e) of Provisional Application No. 60/137,501, filed Jun. 4, 1999, now abandoned. The contents of each of these applications are entirely incorporated by reference herein.

BACKGROUND OF THE INVENTION

1. Field of the Invention

This invention is in the field of medicinal chemistry. In particular, the invention relates to the use of substituted 5-oxo-5,6,7,8-tetrahydro-4H-1-benzopyrans as positive modulators of AMPA receptors, and for the treatment of neurodegenerative conditions, for the treatment of schizophrenia, and as cognitive enhancers.

2. Related Background Art

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonist N-methyl-aspartate (NMDA), α-amino-3-hydroxy-5-methyoisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic connections during development, but also changes in the efficiency of synaptic transmission throughout life. See Schoepp, Bockaert, and Sladeczek, *Trends Pharm. Sci.* 11: 508 (1990); McDonald and Johnson, *Brain Res. Rev.* 15: 41 (1990).

There is much evidence suggesting that the interaction of glutamate with membrane receptors plays a key role on many critical neurological functions such as cognition, learning and memory. Cognitive deficits likely arising from hypoactivity of glutamate receptors are known to be associate with neurodegenerative disorders such as Alzheimer's disease. Hypoactivity of glutamate receptors also might be associated with schizophrenia. One therapeutic approach is the direct stimulation of glutamate receptors with agonists. However, this approach increases the risk of excitotoxicity and may lead to further neurodegeneration. Selective positive modulation of certain glutamate receptor subtypes would be a better approach. Therefore positive modulators of AMPA receptors are expected to be useful for the treatment or amelioration of a number of chronic neurologic disorders such as schizophrenia, Alzheimer's disease and malnutrition, as well as neural maldevelopment (Thomas, R. J., *J. Am. Geriatr. Soc.* 43:1279–1289 (1995)). It has been shown that the AMPA receptor positive modulator BDP 1-(1,3-benzodioxol-5-ylcarbonyl)piperidine and its derivatives enhance memory in rat (Staubli et al., *Proc. Natl. Acad. Sci.* 91:777–778 (1994)). The AMPA-positive modulator BDP-29 also has been shown to attenuate the amount of stereotypic rearings seen in rats after methamphetamine injection, suggesting that AMPA receptor modulators might be useful for the treatment of schizophrenia (Larson et al., *Brain Res.* 738:353–356 (1996)). Furthermore, piracetam, a well-known nootropic agent, which is used to treat cognitive impairment in the elderly, was found to be a positive modulator of AMPA receptors (Copani et al., *J. Neurochem.* 58:1199–1204 (1992)). A recent clinical study showed that piracetam was effective in treating patients with myoclonus, especially that of cortical origin (Ikeda et al., *Movement Disorders* 11:691–700 (1996)). Thus, AMPA receptor positive modulators are expected to be useful in treating myoclonus.

Desai et al. (*Neurophamacology* 34:141–147 (1995)) reported that the memory-enhancing agent 1-BCP selectively potentiates AMPA-induced [$^3$H]norepinephrine release in rat hippocampal slices.

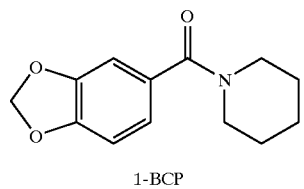

1-BCP

Zivkovic et. al. (*J. Pharmacol. Exp. Therap*, 272:300–309 (1995)) reported that the cognitive enhancer IDRA 21 attenuates AMPA receptor desensitization.

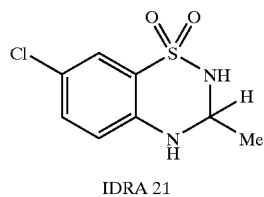

IDRA 21

Yamada et. al (*Brit. J. Pharmacol*, 117:1663–1672 (1996)) reported that cyclothiazide blocks AMPA receptor desensitization and potentiates AMPA receptor gated currents.

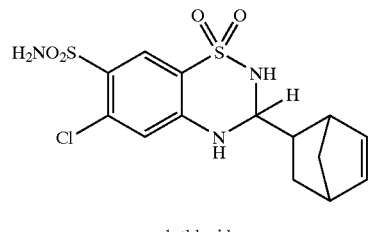

cyclothlazide

SUMMARY OF THE INVENTION

The invention relates to the discovery that the compounds represented by Formula I are positive modulators of α-amino-3-hydroxy-5-methyoisoxazole-4-propionic acid (AMPA) receptors. A first aspect of the invention is directed to method for treating a disorder responsive to the positive modulation of AMPA receptors in animals suffering therefrom, comprising administering to an animal in need thereof a compound of Formula I:

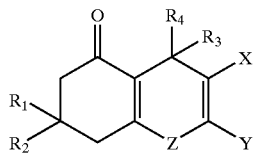

or a pharmaceutically acceptable salt or prodrug thereof, wherein:

$R_1$ and $R_2$ are independently hydrogen, $C_{1-10}$ alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl or thioalkyl; or $R_1$ and $R_2$ are taken together to form a carbocycle or heterocycle;

$R_3$ is hydrogen, or $C_{1-10}$ alkyl;

$R_4$ is substituted or unsubstituted aryl or heteroaryl, carbocycle or heterocycle;

X is hydrogen, $NO_2$, CN, $C_{1-10}$ alkyl, haloalkyl, aryl, heteroaryl, COR, $CO_2R$ and $CONR_xR_y$, wherein R, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together to form a heterocycle;

Y is $NH_2$, NHR, and NHCOR; and

Z is O and S.

These compounds can be used as cognitive enhancers, for the treatment of neurodegenerative diseases, including Alzheimer's disease, amyotrophic lateral sclerosis, Huntington's disease, Parkinson's disease, AIDS associated dementia and Down's syndrome as well as for the treatment of schizophrenia and myoclonus. A further aspect of the present invention is to provide a method for treating, preventing or ameliorating neurodegenerative diseases, including Alzheimer's disease, amyotrophic lateral sclerosis, Huntington's disease, Parkinson's disease, AIDS associated dementia and Down's syndrome as well as for the treatment of schizophrenia and myoclonus by administering a compound of Formula I to a mammal in need of such treatment.

A further aspect of the present invention is to provide a pharmaceutical composition useful for treating disorders responsive to the positive modulation of AMPA receptors, comprising an effective amount of a compound of Formula I in a mixture with one or more pharmaceutically acceptable carriers or diluents.

A number of compounds useful in the present invention have not been heretofor reported. Thus, the present invention is also directed to novel substituted 5-oxo-5,6,7,8-tetrahydro-4H-1-benzopyrans of Formula I. Further, the present invention is directed to $^3H$ and $^{14}C$ radiolabeled compounds of Formula I and their use as radioligands for their binding site on the sodium channel.

DETAILED DESCRIPTION OF THE INVENTION

Figure 1:
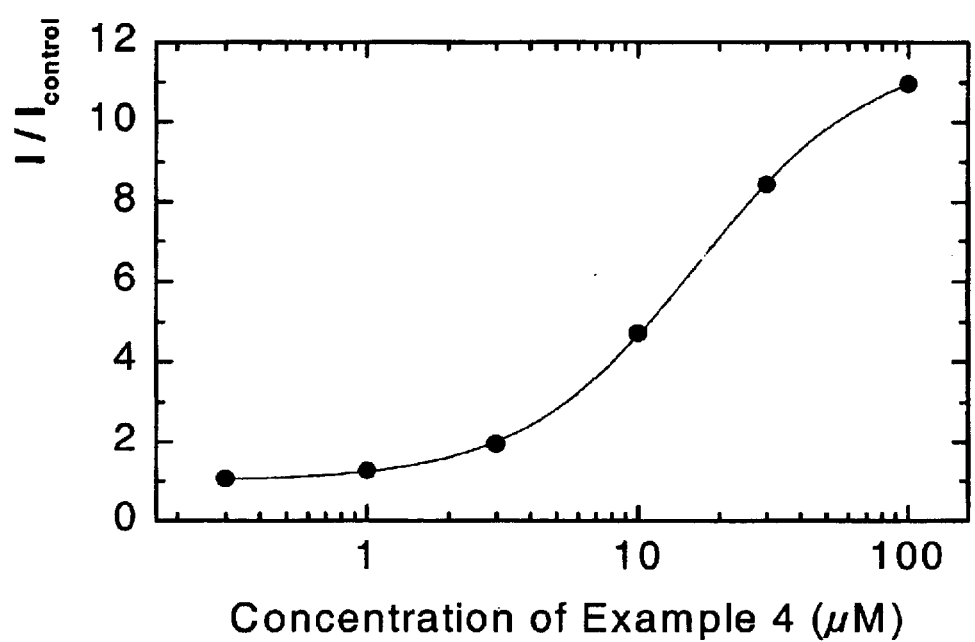
FIG. 1 depicts a graph showing the concentration-effect relationship for the potentiation of AMPA-evoked currents in Xenopus oocytes by the compound of Example 4. Xenopus oocytes were injected with rat cortical poly (A+) RNA and membrane currents were measured by a standard, two-microelectrode voltage clamp method. A solution of AMPA (10 μM) was superfused through the recording chamber in the absence (control) or presence of increasing concentrations of the compound of Example 4. "T" is membrane current.

The substituted 5-oxo-5,6,7,8-tetrahydro-4H-1-benzopyrans and benzothiopyrans are represented by Formula I. Generally, preferred structures of the substituted 5-oxo-5,6,7,8-tetrahydro-4H-1-benzopyrans are those compounds where $R_1$ and $R_2$ are each hydrogen or are each methyl, preferably methyl. More preferred compounds are those where $R_3$ is hydrogen and $R_4$ is optionally substituted aryl. Even more preferred are compounds above where X is CN, Y is $NH_2$ and Z is O. Preferred structures of the substituted 5-oxo-5,6,7,8-tetrahydro-4H-1-benzopyrans of and useful in the present invention are represented by Formulae II–VI. Thus, preferred embodiments are represented by Formula II:

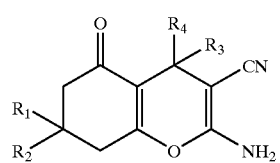

or a pharmaceutically acceptable salt or prodrug thereof;

Formula III:

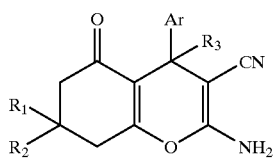

or a pharmaceutically acceptable salt or prodrug thereof;

Formula IV:

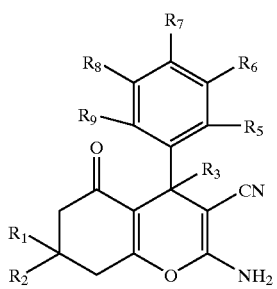

or a pharmaceutically acceptable salt or prodrug thereof;

Formula V:

$$\text{V}$$

or a pharmaceutically acceptable salt or prodrug thereof;
Formula VI:

$$\text{VI}$$

or a pharmaceutically acceptable salt or prodrug thereof;
wherein $R_1$, $R_2$, $R_3$ and $R_4$ are as defined previously with respect to Formula I;

$R_5$–$R_9$ are independently hydrogen, halo, haloalkyl, aryl, fused aryl, a carbocyclic group, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol; or $R_5$ and $R_6$, or $R_6$ and $R_7$ are taken together to form a carbocycle or heterocycle, including —OCH$_2$O—, —OCF$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —CH=CH—CH=CH— and —N=CH—CH=N—.

With respect to the formulae above:

Optional substituents on the aryl, aralkyl, aryloxy, arylthioxy, aroyl, heterocyclic, heterocycloxy, heteroaryl, heteroaryloxy, cycloalkyl, and cycloalkoxy groups listed above can include one or more of halo, haloalkyl, aryl, fused aryl, heterocyclic, heteroaryl, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamino, hydroxy, thiol, acyloxy, azido, alkoxy, carboxy, carbonylamido, and alkylthiol groups mentioned above.

Preferred optional substituents on optionally substituted groups include one or more groups independently selected from the group consisting of halo, halo($C_{1-6}$)alkyl, aryl, pyrimidine, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro, amino, ureido, cyano, $C_{1-6}$ acylamino, hydroxy, thiol, $C_{1-6}$ acyloxy, azido, $C_{1-6}$ alkoxy, carboxy, aminocarbonyl, carbamoyloxy, $C_{1-6}$ alkylsulfonylamino, $C_{1-6}$ acyl, and $C_{1-6}$ alkylthiol groups mentioned above as long as the resulting compound is stable. More preferred optional substituents include: halo, halo($C_{1-6}$)alkyl, hydroxy($C_{1-6}$)alkyl, amino($C_{1-6}$)alkyl, hydroxy, nitro, $C_{1-6}$ alkyl, $C_{1-6}$alkoxy, aminocarbonyl, carbamoyloxy, $C_{1-6}$ alkylsulfonylamino, $C_{1-6}$ acyl and amino.

Preferred compounds of, and for use in, the present invention include compounds where Z is O; particularly when X is CN and Y is NH$_2$.

Preferred values of $R_1$ and $R_2$ include hydrogen, $C_{1-6}$ alkyl, $C_{1-6}$ haloalkyl, $C_{1-6}$ hydroxyalkyl, $C_{1-6}$ aminoalkyl, or $C_{1-6}$ thioalkyl, more preferable hydrogen or $C_{1-6}$ alkyl. Most preferably, $R_1$ and $R_2$ are both hydrogen or are both methyl.

Preferred values of $R_4$ are optionally substituted phenyl, naphthyl and pyridyl, more preferably optionally substituted phenyl. Suitable values of $R_4$ are 4-methoxyphenyl, 2,4,6-trimethylphenyl, phenyl, 3,4-methylenedioxyphenyl, 4-methoxyphenyl, 4-chlorophenyl, 3-hydroxyphenyl, 4-methylphenyl, 4-dimethylaminophenyl, 4-hydroxyphenyl, 3-methoxyphenyl, 4-nitrophenyl, 5-methoxy-3,4-methylenedioxyphenyl, 3,4-difluoromethylenedioxyphenyl, 4-cyanophenyl, 4-fluorophenyl, 2-naphthyl, and 3-chlorophenyl.

A preferred subgenus of, and useful in, the present invention includes compounds of Formula I, or a pharmaceutically acceptable salt thereof, wherein:

$R_1$ and $R_2$ are independently hydrogen, $C_{1-6}$ alkyl, $C_{1-6}$ haloalkyl, $C_{1-6}$ hydroxyalkyl, $C_{1-6}$ aminoalkyl, $C_{1-6}$ thioalkyl $C_{1-10}$ aryl, $C_{4-7}$ cycloalkyl, $C_{2-6}$ alkenyl, $C_{2-6}$ alkynyl, $C_{6-10}$ aryl($C_{1-6}$)alkyl, $C_{6-10}$ aryl($C_{2-6}$)alkenyl, $C_{6-10}$ aryl($C_{2-6}$)alkynyl, or $C_{4-7}$ cycloalkyl($C_{1-6}$)alkyl; or $R_1$ and $R_2$ are taken together with the carbon atom to which they are attached to form a $C_{3-7}$ cycloalkyl or a 5 or 6 membered heterocycle having one or two of N, S, O or a combination thereof;

$R_3$ is hydrogen, or $C_{1-6}$ alkyl;

$R_4$ is an optionally substituted $C_{6-10}$ aryl, heteroaryl, carbocycle or heterocycle;

X is hydrogen, NO$_2$, CN, $C_{1-10}$ alkyl, haloalkyl, aryl, heteroaryl, COR, CO$_2$R or CONR$_x$R$_y$, wherein R, R$_x$ and R$_y$ are independently hydrogen, $C_{1-10}$ alkyl, haloalkyl, aryl, fused aryl, a carbocyclic group, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or R$_x$ and R$_y$ are taken together to form a heterocycle;

Y is NH$_2$, NHR, or NHCOR, where R is as defined above; and

Z is O or S.

Exemplary preferred compounds that may be employed in the compositions and methods of invention include, without limitation:

2-amino-3-cyano-7,7-dimethyl-4-(4-methoxyphenyl)-5-oxo-5,6,7,8-tetrahydro-4H-1-benzopyran;

2-amino-3-cyano-7,7-dimethyl-4-(2,4,6-trimethylphenyl)-5-oxo-5,6,7,8-tetrahydro-4H-1-benzopyran;

2-amino-3-cyano-7,7-dimethyl-4-phenyl-5-oxo-5,6,7,8-tetrahydro-4H-1-benzopyran;

2-amino-3-cyano-7,7-dimethyl-4-(3,4-methylenedioxyphenyl)-5-oxo-5,6,7,8-tetrahydro-4H-1-benzopyran;

2-amino-3-cyano-4-(4-methoxyphenyl)-5-oxo-5,6,7,8-tetrahydro-4H-1-benzopyran;

2-amino-3-cyano-7,7-dimethyl-4-(4-chlorophenyl)-5-oxo-5,6,7,8-tetrahydro-4H-1-benzopyran;

2-amino-3-cyano-7,7-dimethyl-4-(3-hydroxyphenyl)-5-oxo-5,6,7,8-tetrahydro-4H-1-benzopyran;

2-amino-3-cyano-7,7-dimethyl-4-(4-methylphenyl)-5-oxo-5,6,7,8-tetrahydro-4H-1-benzopyran;

2-amino-3-cyano-7,7-dimethyl-4-(4-dimethylaminophenyl)-5-oxo-5,6,7,8-tetrahydro-4H-1-benzopyran;

2-amino-3-cyano-7,7-dimethyl-4-(4-hydroxyphenyl)-5-oxo-5,6,7,8-tetrahydro-4H-1-benzopyran;

2-amino-3-cyano-7,7-dimethyl-4-(3-methoxyphenyl)-5-oxo-5,6,7,8-tetrahydro-4H-1-benzopyran;

2-amino-3-cyano-7,7-dimethyl-4-(4-nitrophenyl)-5-oxo-5,6,7,8-tetrahydro-4H-1-benzopyran;

2-amino-3-cyano-7,7-dimethyl-4-(4-pyridyl)-5-oxo-5,6,7,8-tetrahydro-4H-1-benzopyran;

2-amino-3-cyano-7,7-dimethyl-4-(5-methoxy-3,4-methylenedioxyphenyl)-5-oxo-5,6,7,8-tetrahydro-4H-1-benzopyran;

2-amino-3-cyano-7,7-dimethyl-4-(3,4-difluoromethylenedioxyphenyl)-5-oxo-5,6,7,8-tetrahydro-4H-1-benzopyran;

2-amino-3-cyano-7,7-dimethyl-4-(4-cyanophenyl)-5-oxo-5,6,7,8-tetrahydro-4H-1-benzopyran;

2-amino-3-cyano-7,7-dimethyl-4-(4-fluorophenyl)-5-oxo-5,6,7,8-tetrahydro-4H-1-benzopyran;

2-amino-3-cyano-7,7-dimethyl-4-(2-naphthyl)-5-oxo-5,6,7,8-tetrahydro-4H-1-benzopyran; and 2-amino-3-cyano-7,7-dimethyl-4-(3-chlorophenyl)-5-oxo-5,6,7,8-tetrahydro-4H-1-benzopyran;

or a pharmaceutically acceptable salt or prodrug thereof.

Novel compounds of the present invention include compounds of Formula IV.

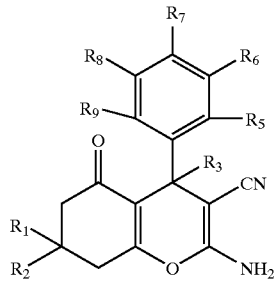

IV or a pharmaceutically acceptable salt or prodrug thereof, wherein:

$R_1$ and $R_2$ are independently hydrogen, $C_{1-6}$ alkyl, $C_{1-6}$ haloalkyl, $C_{1-6}$ hydroxyalkyl, $C_{1-6}$ aminoalkyl, $C_{1-6}$ thioalkyl $C_{6-10}$ aryl, $C_{4-7}$ cycloalkyl, $C_{2-6}$ alkenyl, $C_{2-6}$ alkynyl, $C_{6-10}$ aryl($C_{1-6}$)alkyl, $C_{6-10}$ aryl($C_{2-6}$)alkenyl, $C_{6-10}$ aryl($C_{2-6}$)alkynyl, or $C_{4-7}$ cycloalkyl($C_{1-6}$)alkyl; or $R_1$ and $R_2$ are taken together with the carbon atom to which they are attached to form a $C_{3-7}$ cycloalkyl or a 5 or 6 membered heterocycle having one or two of N, S, O or a combination thereof;

$R_3$ is hydrogen, or $C_{1-6}$ alkyl; and $R_5$–$R_9$ are independently hydrogen, halo, haloalkyl, aryl, fused aryl, a carbocyclic group, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, acyloxy, azido, alkoxy, carboxy, carbonylamido or alkylthiol;

Preferably, $R_5$ and $R_6$ are taken together with the carbon atoms to which they are attached, or $R_6$ and $R_7$ are taken together with the carbon atoms to which they are attached form a carbocycle or heterocycle.

Preferably, $R_5$ and $R_6$ taken together are with the carbon atoms to which they are attached to form one of —OCH$_2$O—, —OCF$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(Me)—C(O)O—, —CH=CH—CH=CH—, or —N=CH—CH=N—, where R is defined above.

Alternatively, $R_6$ and $R_7$ taken together are with the carbon atoms to which they are attached to form one of —OCH$_2$O—, —OCF$_2$O—, —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —N(Me)—C(O)—O—, —CH=CH—CH=CH—, or —N=CH—CH=N—, where R is defined above.

Novel compounds of the present invention include:

2-amino-3-cyano-7,7-dimethyl-4-(2,4,6-trimethylphenyl)-5-oxo-5,6,7,8-tetrahydro-4-H-1-benzopyran;

2-amino-3-cyano-7,7-dimethyl-4-(3,4-methylenedioxyphenyl)-5-oxo-5,6,7,8-tetrahydro-4-H-1-benzopyran;

2-amino-3-cyano-7,7-dimethyl-4-(4-methylphenyl)-5-oxo-5,6,7,8-tetrahydro-4-H-1-benzopyran;

2-amino-3-cyano-7,7-dimethyl-4-(4-dimethylaminophenyl)-5-oxo-5,6,7,8-tetrahydro-4-H-1-benzopyran;

2-amino-3-cyano-7,7-dimethyl-4-(-3-methoxyphenyl)-5-oxo-5,6,7,8-tetrahydro-4-H-1-benzopyran;

2-amino-3-cyano-7,7-dimethyl-4-(4-pyridyl)-5-oxo-5,6,7,8-tetrahydro-4-H-1-benzopyran;

2-amino-3-cyano-7,7-dimethyl-4-(5-methoxy-3,4-methylenedioxyphenyl)-5-oxo-5,6,7,8-tetrahydro-4-H-1-benzopyran; and 2-amino-3-cyano-7,7-dimethyl-4-(3,4-difluoromethylenedioxyphenyl)-5-oxo-5,6,7,8-tetrahydro-4-H-1-benzopyran;

2-amino-3-cyano-7,7-dimethyl-4-(4-cyanophenyl)-5-oxo-5,6,7,8-tetrahydro-4-H-1-benzopyran;

and a pharmaceutically acceptable salt or prodrug thereof.

With respect to the present invention, the following definitions apply, unless otherwise explicitly provided for.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, pteridinyl, 4aH-carbazolyl, carbazolyl, β-carbolinyl, phenanthridinyl, acridinyl, perimidinyl, phenanthrolinyl, phenazinyl, thiazolyl, isothiazolyl, phenothiazinyl, isoxazolyl, furazanyl, and phenoxazinyl groups). Suitable heteroaryl groups include pyridyl, furanyl and thienyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{1-6}$ alkenyl groups, preferably $C_{1-6}$ alkenyl. Typical $C_{1-6}$ alkenyl groups include ethenyl, propenyl, isopropenyl, butenyl, and sec-butenyl.

Useful alkynyl groups are $C_{2-6}$ alkynyl groups, preferably $C_{2-4}$ alkynyl. Typical $C_{2-4}$ alkynyl groups include ethynyl, propynyl, butynyl, and 2-butynyl groups.

Useful arylalkyl (or aralkyl) groups include any of the above-mentioned $C_{1-10}$ alkyl groups substituted by any of the above-mentioned $C_{6-14}$ aryl groups. Useful values include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful heteroarylalkyl groups include any of the above-mentioned $C_{1-10}$ alkyl groups substituted by any of the above-mentioned heteroaryl groups.

Useful heteroarylalkenyl groups include any of the above-mentioned $C_{2-4}$ alkenyl groups substituted by any of the above-mentioned heteroaryl groups.

Useful heteroarylalkynyl groups include any of the above-mentioned $C_{2-4}$ alkynyl groups substituted by any of the above-mentioned heteroaryl groups.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

The term heterocycle is used herein to mean saturated or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperazine, morpholine, imidazoline, pyrazolidine, benzodiazepines and the like.

Useful heterocycloalkyl groups include any of the above-mentioned $C_{1-10}$ alkyl groups substituted by any of the above-mentioned heterocyclic groups.

Useful alkylamino and dialkylamino groups are —$NHR_{20}$ and —$NR_{20}R_{21}$, wherein $R_{20}$ and $R_2$, are $C_{1-10}$ alkyl groups.

Aminocarbonyl group is —$C(O)NH_2$.

Useful alkylaminocarbonyl groups are carbonyl groups substituted by —$NHR_{20}$ and —$NR_{20}R_{21}$, wherein $R_{20}$ and $R_{21}$ are $C_{1-10}$ alkyl groups as defined above.

Useful alkylthiol groups include any of the above-mentioned $C_{1-10}$ alkyl groups substituted by a —SH group.

A carbamoyloxy group is —O—C(O)—$NH_2$.

A carboxy group is —COOH.

An azido group is —$N_3$.

An ureido group is —NH—C(O)$NH_2$.

An amino group is —$NH_2$.

An amide group is an organic radical having —NHC(O)— as a functional group.

Certain of the compounds of the present invention may exist as optical isomers and the invention includes both the racemic mixtures of such optical isomers as well as the individual entantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate.

Examples of prodrugs include esters or amides of Formula I with $R_3$ as hydroxyalkyl or aminoalkyl, by reacting such compounds with an anhydride such as succinic anhydride.

The invention disclosed herein is meant to encompass all pharmaceutically acceptable salts thereof of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass prodrugs of the disclosed compounds. Prodrugs are considered to be any covalently bonded carriers which release the active parent drug in vivo. Examples of prodrugs include esters or amides of Formula I with $R_1$–$R_9$ as hydroxyalkyl or aminoalkyl, and these may be prepared by reacting such compounds with anhydrides such as succinic anhydride.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Some of the compounds disclosed herein may contain one or more asymmetric centers and may thus give rise to enantiomers, diastereomers, and other stereoisomeric forms.

The present invention is also meant to encompass racemic mixtures, resolved forms mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal pails of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The invention is also directed to $^3$H and $^{14}$C radiolabeled compounds of Formula I and their use as radioligands for their binding site on the sodium channel. For example, one use of the labeled compounds of the invention is the characterization of specific receptor binding. Another use of the labeled compounds of the invention is an alternative, to animal testing for the evaluation of structure-activity relationships. The receptor assay is performed at a fixed concentration of a labeled compound of Formula I and at increasing concentrations of a test compound in a competition assay.

Tritiated compounds of Formula I can be prepared by introducing tritium into the compound of Formula I by, for example, catalytic dehalogenation with tritium. This method includes reacting a suitably halogen-substituted precursor of a compound of Formula I with tritium gas in the presence of a suitable catalyst, for example Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6. $^{14}$C-labeled compounds can be prepared by employing starting materials having a $^{14}$C carbon.

Also included within the scope of the present invention are the non-toxic pharmaceutically acceptable salts of the compounds of the present invention. Acid addition salts are formed by mixing a solution of the particular heteroaryl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the heteroaryl compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among such animals are mammals, e.g., humans, although the invention is not intended to be so limited.

The compounds of this invention may be prepared using methods well known to those skilled in the art, such as those described by Abdel-Latif et al. (*J. Chem. Res. Miniprint*, 5, 1220–1228 (1995)) or by the novel methods of this invention. Exemplary reactions are illustrated in Equations 1–4. The starting materials employed in Equations 1–4 are readily available or can be prepared by known methods.

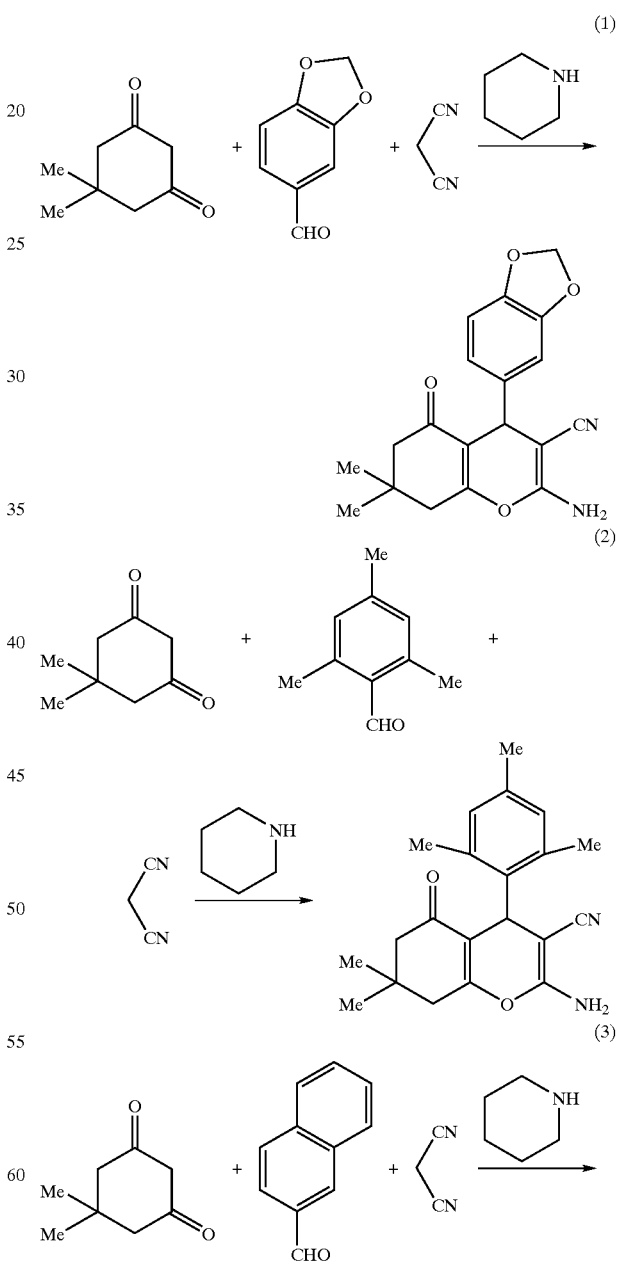

-continued

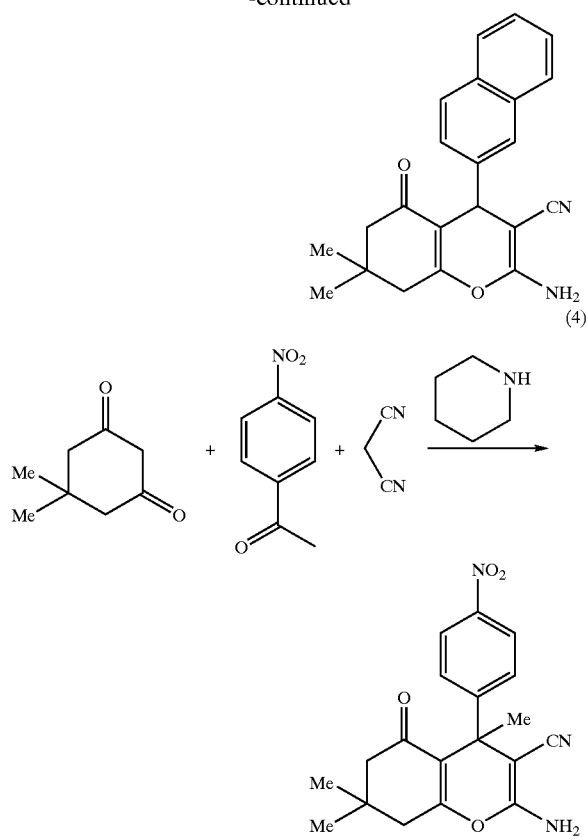

The novel compounds of the invention were assessed by electrophysiological assays in Xenopus oocytes expressing rat whole brain poly(A)$^+$ RNA (see Keana et al, *J. Med. Chem.* 38: 4367–4379 (1995)) or in cultured rat cortical neurons (see Woodward et al., *Mol. Pharmacol.* 47: 568–581 (1995)) for AMPA receptor activity. The compounds that potentiate currents across the oocyte membrane are expected to be useful as cognitive enhancers or for the treatment of schizophrenia, myoclonus or neurodegenerative diseases such as Parkinson's disease and Alzheimer's disease. Thus, the present invention is directed to compounds that are positive modulators of AMPA receptors.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for psychosis disorders. Preferably, about 0.01 to about 10 mg/kg is orally administered to treat or prevent such disorders. For intramuscular injection, the dose is generally about one-half of the oral dose.

For the treatment of AIDS associated neuronal damage, Alzheimer's disease, amyotrophic lateral sclerosis, Huntington's disease and Down's Syndrome, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular AMPA positive modulator of the present invention with a solution of a pharmaceutically acceptable non-toxic acid such as hydrochloric acid, fumaric acid, maleic acid, succinic acid, acetic acid, dichloroacetic acid, citric acid, tartaric acid, carbonic acid, phosphoric acid, oxalic acid, and the like. Basic salts are formed by mixing a solution of the particular AMPA positive modulator of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEGA-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of non-competitive AMPA receptors modulators in vitro has been difficult because of the lack of selective drug ligands. Thus, the AMPA ligands of the present invention may be used to characterize the AMPA receptors and their distribution. Particularly preferred AMPA positive modulator of the present invention which may be used for this purpose are isotopically radiolabelled derivatives, e.g. where one or more of the atoms are replaced with $^3H$, $^{11}C$, $^{14}C$ or $^{18}F$. Alternatively, a fluorescent group Y may be employed. Examples of such groups include 4-nitrobenzofurazan.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

2-Amino-3-cyano-7,7-dimethyl-4-(4-methoxyphenyl)-5-oxo-5,6,7,8-tetrahydro-4H-1-benzopyran A stirred solution of p-anisaldehyde (1.74 mL, 14.3 mmol) and malononitrile (0.90 mL, 14.28 mmol) in 75 mL of 95% EtOH at RT was treated with a few drops of piperidine and after about 5 min, a yellow precipitate was formed and the mixture was stirred for another 10 min after which 5,5-dimethylcyclohexan-1,3-dione (2.00 g, 14.3 mmol) was added as a solid in one portion. The stirred suspension became a solution after about 5 min. After about 2 h a white precipitate was formed and TLC analysis showed complete reaction. The precipitate was filtered and washed with cold 95% EtOH then dried under vacuum, resulting in 3.71 g (81%) of the title compound as a white solid, mp 197–200° C. $^1H$ NMR (DMSO-$d_6$): 7.04 (d, 2H), 6.96 (bs, 2H), 6.83 (d, 2H), 4.11 (s, 1H), 3.71 (s, 3H), 2.49 (m, 2H), 2.15 (m, 2H), 1.03 (s, 3H), 0.94 (s, 3H).

EXAMPLES 2–18

2. 2-Amino-3-cyano-7,7-dimethyl-4-(2,4,6-trimethylphenyl)-5-oxo-5,6,7,8-tetrahydro-4H-1-benzopyran: The title compound was synthesized (4.1 g, 85%) as a white solid from 2,4,6-trimethylbenzaldehyde (14.3 mmol) using the same procedure described in Example 1. $^1H$ NMR (DMSO-$d_6$): 6.90 (bs, 2H), 6.79 (s, 1H), 6.70 (s, 1H), 4.73 (s, 1H), 2.45 (m, 4H), 2.15 (s, 6H), 2.09 (s, 3H), 1.01 (s, 3H), 0.99 (s, 3H).

3. 2-Amino-3-cyano-7,7-dimethyl-4-phenyl-5-oxo-5,6,7,8-tetrahydro-4H-1-benzopyran: The title compound was synthesized (770 mg, 73%) as an off-white solid from benzaldehyde (3.57 mmol) using the same procedure described in Example 1, mp 228–233° C. $^1H$ NMR (DMSO-$d_6$): 7.28 (m, 2H), 7.15 (m, 3H), 7.01 (bs, 2H), 4.17 (s, 1H), 2.52 (m, 2H), 2.17 (m, 2H), 1.04 (s, 3H), 0.95 (s, 3H).

4. 2-Amino-3-cyano-7,7-dimethyl-4-(3,4-methylenedioxyphenyl)-5-oxo-5,6,7,8-tetrahydro-4H-1-benzopyran: The title compound was synthesized (828 mg, 69%) as a light yellow solid from piperonal (3.57 mmol) using the same procedure described in Example 1, mp 209–212° C. $^1H$ NMR (DMSO-$d_6$): 6.98 (bs, 2H), 6.81 (d, 1H), 6.65 (d, 1H), 6.61 (dd, 1H), 5.97 (s, 2H), 4.11 (s, 1H), 2.50 (s, 2H), 2.18 (m, 2H), 1.03 (s, 3H), 0.96 (s, 3H).

5. 2-Amino-3-cyano-4-(4-methoxyphenyl)-5-oxo-5,6,7,8-tetrahydro-4H-1-benzopyran: The title compound was synthesized (550 mg, 69%) as an off-white solid from p-anisaldehyde (2.68 mmol) and 1,3-cyclohexanedione (2.68 mmol) in place of 5,5-dimethyl-1,3-cyclohexanedione using the same procedure described in Example 1, mp 209–212° C. $^1H$ NMR (DMSO-$d_6$): 7.06 (d, 2H), 6.96 (bs, 2H), 6.83 (d, 2H), 4.13 (s, 1H), 3.71 (s, 3H), 2.60 (m, 2H), 2.25 (m, 2H), 1.90 (m, 2H).

6. 2-Amino-3-cyano-4-(4-chlorophenyl)-7,7-dimethyl-5-oxo-5,6,7,8-tetrahydro-4H-1-benzopyran: The title compound was synthesized (1.057 g, 90%) as a white solid from 4-chlorobenzaldehyde (3.57 mmol) using the same procedure described in Example 1, mp 212–214° C., $^1$H NMR (DMSO-$d_6$): 7.35 (d, 2H), 7.16 (d, 2H), 7.07 (bs, 2H), 4.19 (s, 1H), 2.51 (m, 2H), 2.17 (m, 2H), 1.03 (s, 3H), 0.94 (s, 3H).

7. 2-Amino-3-cyano-7,7-dimethyl-4-(3-hydroxyphenyl)-5-oxo-5,6,7,8-tetrahydro-4H-1-benzopyran: The title compound was synthesized (750 mg, 68%) as a white solid from 3-hydroxybenzaldehyde (3.57 mmol) using the same procedure described in Example 1, mp 214–217° C., $^1$H NMR (DMSO-$d_6$); 9.31 (s, 1H), 7.05 (m, 1H), 6.97 (bs, 2H), 6.55 (s, 3H), 4.07 (s, 1H), 2.50 (m, 2H), 2.18 (m, 2H), 1.04 (s, 3H), 0.96 (s, 3H).

8. 2-Amino-3-cyano-7,7-dimethyl-4-(4-methylphenyl)-5-oxo-5,6,7,8-tetrahydro-4H-1-benzopyran: The title compound was synthesized (982 mg, 89%) as a white solid from 4-methylbenzaldehyde (3.57 mmol) using the same procedure described in Example 1, mp 219–221° C., $^1$H NMR (DMSO-$d_6$): 7.08 (d, 2H), 7.01 (d, 2H), 6.96 (bs, 2H), 4.12 (s, 1H), 2.50 (m, 2H), 2.24 (s, 3H), 2.16 (m, 2H), 1.03 (s, 3H), 0.95 (s, 3H).

9. 2-Amino-3-cyano-7,7-dimethyl-4-(4-dimethylaminophenyl)-5-oxo-5,6,7,8-tetrahydro-4H-1-benzopyran: The title compound was synthesized from 4-dimethylaminobenzaldehyde (3.57 mmol) using the same procedure described in Example 1, with the addition of heating for 5 h after adding the dione, resulting in 1.026 g (85%) of the compound as a pale orange solid, mp 221–224° C., $^1$H NMR (DMSO-$d_6$): 6.93 (d, 2H), 6.88 (bs, 2H), 6.62 (d, 2H), 4.04 (s, 1H), 2.84 (s, 6H), 2.48 (m, 2H), 2.15 (m, 2H), 1.03 (s, 3H), 0.94 (s, 3H).

10. 2-Amino-3-cyano-7,7-dimethyl-4-(4-hydroxyphenyl)-5-oxo-5,6,7,8-tetrahydro-4H-1-benzopyran: The title compound was synthesized (870 mg, 79%) as a white solid from 4-hydroxybenzaldehyde (3.57 mmol) using the same procedure described in Example 1, mp 207–210° C., $^1$H NMR (DMSO-$d_6$): 9.25 (d, 1H), 6.91 (m, 4H), 6.64 (m, 2H), 4.0 (s, 1H), 2.48 (m, 2H), 2.15 (m, 2H), 1.02 (s, 3H), 0.94 (s, 3H).

11. 2-Amino-3-cyano-7,7-dimethyl-4-(3-methoxyphenyl)-5-oxo-5,6,7,8-tetrahydro-4H-1-benzopyran: The title compound was synthesized (840 mg, 73%) as a white solid from 3-methoxybenzaldehyde (3.57 mmol) using the same procedure described in Example 1, mp 198–201° C., $^1$H NMR (DMSO-$d_6$): 7.20 (t, 1H), 7.00 (bs, 2H), 6.73 (m, 2H), 6.65 (s, 1H), 4.14 (s, 1H), 3.71 (s, 3H), 2.52 (m, 2H), 2.18 (m, 2H), 1.04 (s, 3H), 0.96 (s, 3H).

12. 2-Amino-3-cyano-7,7-dimethyl-4-(4-nitrophenyl)-5-oxo-5,6,7,8-tetrahydro-4H-1-benzopyran: The title compound was synthesized (0.84 g, 90%) as a yellow solid from 4-nitrobenzaldehyde (3.57 mmol) using the same procedure described in Example 1, mp 177–180° C., $^1$H NMR (DMSO-$d_6$): 8.17 (d, 2H), 7.44 (d, 2H), 7.19 (bs, 2H), 4.36 (s, 1H), 2.54 (m, 2H), 2.18 (m, 2H), 1.04 (s, 3H), 0.96 (s, 3H).

13. 2-Amino-3-cyano-7,7-dimethyl-4-(4-pyridyl)-5-oxo-5,6,7,8-tetrahydro-4H-1-benzopyran: The title compound was synthesized (593 mg, 56%) as a white solid from pyridine-4-carboxaldehyde (3.57 mmol) using the same procedure described in Example 1, mp 222–224° C., $^1$H NMR (DMSO-$d_6$): 8.48 (d, 2H), 7.15 (bs, 4H), 4.20 (s, 1H), 2.53 (s, 2H), 2.19 (m, 2H), 1.04 (s, 3H), 0.97 (s, 3H).

14. 2-Amino-3-cyano-7,7-dimethyl-4-(3-methoxy-4,5-methylenedioxyphenyl)-5-oxo-5,6,7,8-tetrahydro-4H-1-benzopyran: The title compound was synthesized (232 mg, 88%) as a yellow solid from 3-methoxy-4,5-methylenedioxybenzaldehyde (0.714 mmol) using the same procedure described in Example 1, mp 239–243° C., $^1$H NMR (DMSO-$d_6$): 6.98 (bs, 2H), 6.37 (s, 1H), 6.32 (s, 1H), 5.95 (s, 2H), 4.11 (s, 1H), 3.79 (s, 3H), 2.51 (s, 2H), 2.19 (m, 2H), 1.03 (s, 3H), 0.98 (s, 3H).

15. 2-Amino-3-cyano-7,7-dimethyl-4-(3,4-difluoromethylenedioxyphenyl)-5-oxo-5,6,7,8-tetrahydro-4H-1-benzopyran: The title compound was synthesized (211 mg, 79%) as a white solid from 3,4-difluoromethylenedioxybenzaldehyde (0.714 mmol) using the same procedure described in Example 1, mp 214–217° C., $^1$H NMR (DMSO-$d_6$): 7.31 (d, 1H), 7.19 (s, 1H), 7.07 (bs, 2H), 6.99 (dd, 1H), 4.25 (s, 1H), 2.51 (m, 2H), 2.17 (m, 2H), 1.03 (s, 3H), 0.96 (s, 3H).

16. 2-Amino-3-cyano-4-(4-cyanophenyl)-7,7-dimethyl-5-oxo-5,6,7,8-tetrahydro-4H-1-benzopyran: The title compound was synthesized (192 mg, 84%) as a pale yellow solid from 4-cyanobenzaldehyde (0.714 mmol) using the same procedure described in Example 1, mp 227–230° C., $^1$H NMR (DMSO-$d_6$): 7.77 (d, 2H), 7.35 (d, 2H), 7.14 (bs, 2H), 4.29 (s, 1H), 2.53 (m, 2H), 2.18 (m, 2H), 1.04 (s, 3H), 0.95 (s, 3H).

17. 2-Amino-3-cyano-7,7-dimethyl-4-(4-fluorophenyl)-5-oxo-5,6,7,8-tetrahydro-4H-1-benzopyran: The title compound was synthesized (87 mg, 39%) as a white solid from 4-fluorobenzaldehyde (0.714 mmol) using the same procedure described in Example 1, mp 189–193° C., $^1$H NMR (DMSO-$d_6$): 7.14 (m, 4H), 7.03 (bs, 2H), 4.19 (s, 1H), 2.51 (m, 2H), 2.17 (m, 2H), 1.03 (s, 3H), 0.94 (s, 3H).

18. 2-Amino-3-cyano-7,7-dimethyl-4-(2-naphthyl)-5-oxo-5,6,7,8-tetrahydro-4H-1-benzopyran: The title compound was synthesized (219 mg, 89%) as a pale yellow solid from 2-naphthaldehyde (0.714 mmol) using the same procedure described in example 1, mp 259–262° C., $^1$H NMR (DMSO-$d_6$): 7.87 (m, 3H), 7.67 (s, 1H), 7.48 (m, 2H), 7.29 (d, 1H), 7.06 (bs, 2H), 4.36 (s, 1H), 2.55 (s, 2H), 2.17 (m, 2H), 1.05 (s, 3H), 0.96 (s, 3H).

EXAMPLE 19

Electrophysiology

Total RNA was prepared from rat cerebral cortex by homogenization in urea/LiCl followed by phenol/chloroform extraction. Polyadenylated (poly A$^+$) mRNA was isolated from total cellular RNA by oligo-dT cellulose chromatography. Xenopus oocytes were prepared by the method of Woodward et al. (Mol. Pharmacol. 41, 89–103 (1992)). Oocytes were microinjected with approximately 50 ng of cortical poly(A)$^+$ RNA and stored in Barth's medium (containing in mM: NaCl, 88; KCl, 1; CaCl$_2$, 0.41; Ca(NO$_3$)$_2$, 0.33; MgSO$_4$, 0.82; NaHCO$_3$, 2.4; HEPES 5; pH 7.4, with 0.1 mg ml gentamycin sulphate) for 6 days prior to recording. Membrane current responses were recorded in frog Ringer solution containing (in mM): NaCl, 115; KCl, 2; CaCl$_2$, 1.8; HEPES, 5; pH 7.4, or in a nominally Ca$^{2+}$-free Ringer solution containing (in mM): NaCl, 115; KCl, 2; BaCl$_2$, 1.8; HEPES, 5; pH 7.4. Electrical recordings were made using a conventional two-electrode voltage clamp (Dagan TEV-200). The oocyte was placed in a 5 ml chamber lined with nylon mesh, impaled with two micro-electrodes and voltage-clamped at a holding potential of −70 mV. A scaled up linear array system (Benveniste and Mayer, J. Physiol. 464, 131–163 (1993)) was used to superfuse the oocyte in Ringer solution and to apply drugs and wash solutions. A control concentration (10 μM) of AMPA was applied to the oocyte to determine a baseline membrane current response. The modulation of this response by AMPA potentiators was measured by applying increasing concentrations of the potentiator in Ringer solution for ~30 s followed by coapplication of the potentiator with 10 µM AMPA. The resulting membrane current responses were analyzed by sigmoidal curve fitting (Origin, Microcal Software, Inc.).

The 5-oxo-5,6,7,8-tetrahydro-4H-1-benzopyrans elicited potentiation of AMPA responses as exemplified by compound of Example 4 (FIG. 1). The maximal potentiation of the AMPA response was 11-fold at 100 µM, and was half-maximally effective at 16.6 µM. A 2-fold potentiation of the AMPA response was elicited at 4 µM for Example 4. The concentration of 5-oxo-5,6,7,8-tetrahydro-4H-1-benzopyrans required for 2-fold potentiation is shown in Table 1.

TABLE 1

Potentiation of AMPA Response by 5-Oxo-5,6,7,8-tetrahydro-4H-1-benzopyrans

| Example # | AMPA positive potentiation 2-fold @ µM |
|---|---|
| 1 | 7.0 |
| 2 | 4.0 |
| 3 | 12.0 |
| 4 | 4.0 |
| 5 | 35.0 |
| 6 | 18.0 |
| 7 | 12.0 |
| 8 | 12.0 |
| 9 | 12.0 |
| 10 | 14.0 |
| 11 | 6.0 |
| 12 | 60.0 |
| 13 | 60.0 |
| 14 | 12.0 |
| 15 | 18.0 |
| 16 | 20.0 |
| 17 | 27.0 |
| 18 | 1.6 |

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound having the Formula I:

IV or a pharmaceutically acceptable salt or prodrug thereof, wherein:

$R_1$ and $R_2$ are independently hydrogen, $C_{1-6}$ alkyl, $C_{1-6}$ haloalkyl, $C_{1-6}$ hydroxyalkyl, $C_{1-6}$ aminoalkyl, $C_{1-6}$ thioalkyl $C_{6-10}$ aryl, $C_{4-7}$ cycloalkyl, $C_{2-6}$ alkenyl, $C_{2-6}$ alkynyl, $C_{6-10}$ aryl($C_{1-6}$)alkyl, $C_{6-10}$ aryl($C_{2-6}$)alkenyl, $C_{6-10}$ aryl($C_{2-6}$)alkynyl, or $C_{4-7}$ cycloalkyl($C_{1-6}$)alkyl; or $R_1$ and $R_2$ are taken together with the carbon atom to which they are attached to form a $C_{3-7}$ cycloalkyl;

$R_3$ is hydrogen or $C_{1-6}$ alkyl; and $R_5$–$R_9$ are independently hydrogen, halo, haloalkyl, aryl, fused aryl, a carbocyclic group, $C_{1-10}$ alkyl, alkenyl, alkynyl, arylalkyl, arylalkenyl, arylalkynyl, carbocycloalkyl, hydroxyalkyl, nitro, amino, cyano, acylamido, hydroxy, thiol, acyloxy, azido, alkoxy, carboxy, carbonylamido or alkylthiol;

provided that $R_5$ and $R_6$ taken together with the carbon atoms to which they are attached form a carbocycle, or $R_6$ and $R_7$ taken together are selected from the group consisting of —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$— and —N=CH—CH=N—;

wherein R is hydrogen, $C_{1-10}$ alkyl, haloalkyl, aryl, fused aryl, a carbocyclic group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl.

2. The compound according to claim 1, wherein $R_1$ and $R_2$ are independently hydrogen, $C_{1-6}$ alkyl, $C_{1-6}$ haloalkyl, $C_{1-6}$ hydroxyalkyl, $C_{1-6}$ aminoalkyl or $C_{1-6}$ thioalkyl.

3. The compound according to claim 1, wherein $R_1$ and $R_2$ are independently hydrogen or $C_{1-6}$ alkyl.

4. The compound according to claim 1, wherein $R_1$ and $R_2$ are both methyl.

5. The compound according to claim 1, wherein $R_1$ and $R_2$ are taken together with the carbon atom to which they are attached to form a $C_{3-7}$ cycloalkyl.

6. The compound according to claim 1, wherein $R_3$ is hydrogen.

7. The compound according to claim 1, wherein $R_3$ is methyl.

8. A compound according to claim 1, wherein $R_5$ and $R_6$ taken together are —OCH$_2$O—, —OCF$_2$O—, —(CH$_2$)$_3$—, —O(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$—, —CH=CH—CH=CH— or —N=CH—CH=N—.

9. The compound according to claim 1, wherein $R_6$ and $R_7$ taken together are selected from the group consisting of —(CH$_2$)$_3$—, —(CH$_2$)$_4$—, —OCH$_2$CH$_2$O—, —CH$_2$N(R)CH$_2$—, —CH$_2$CH$_2$N(R)CH$_2$—, —CH$_2$N(R)CH$_2$CH$_2$— and —N=CH—CH=N—.

10. The compound according to claim 1, wherein $R_5$–$R_9$ are independently hydrogen, halo, haloalkyl, aryl, fused aryl, $C_{1-10}$ alkyl, alkenyl, alkynyl, nitro, amino, cyano, hydroxy or thiol.

11. The compound according to claim 1, wherein $R_6$ and $R_7$ taken together are —OCH$_2$O—.

12. The compound according to claim 1, wherein $R_5$ and $R_6$ taken together are —CH=CH—CH=CH—.

13. The compound according to claim 1, wherein
$R_1$ and $R_2$ are independently hydrogen or $C_{1-6}$ alkyl;
$R_3$ is hydrogen; and
$R_5$ and $R_6$ taken together are —OCH$_2$O—.

14. The compound according to claim 1, wherein
$R_1$ and $R_2$ are independently hydrogen or $C_{1-6}$ alkyl;
$R_3$ is hydrogen; and
$R_6$ and $R_7$ taken together are —CH=CH—CH=CH—.

15. A compound of 2-amino-3-cyano-7,7-dimethyl-4-(2-naphthyl)-5-oxo-5,6,7,8-tetrahydro-4H-1-benzopyran.

16. A compound- of 2-amino-3-cyano-7,7-dimethyl-4-(3-methoxy-4,5-methylenedioxy phenyl)-5-oxo-5,6,7,8-tetrahydro-4H-1-benzopyran.

17. A pharmaceutical composition for treating a disorder responsive to the positive modulation of AMPA receptors in an animal suffering thereof, comprising a compound of claim 1 in an amount effective to positively modulate AMPA receptors in said animal.

18. A pharmaceutical composition for treating a disorder responsive to the positive modulation of AMPA receptors in an animal suffering thereof, comprising a compound of claim 1 in an amount effective to positively modulate AMPA receptors in said animal.

* * * * *